United States Patent [19]

Meth-Cohn et al.

[11] 4,375,544

[45] Mar. 1, 1983

[54] FUSED PYRIDINES

[75] Inventors: Otto Meth-Cohn; Brahma Narine, both of Salford, England

[73] Assignee: Croda Synthetic Chemicals Limited, Four Ashes, Nr. Wolverhampton, England

[21] Appl. No.: 217,325

[22] PCT Filed: Jan. 24, 1979

[86] PCT No.: PCT/GB79/00017

§ 371 Date: Jun. 8, 1979

§ 102(e) Date: Jun. 8, 1979

[87] PCT Pub. No.: WO79/00540

PCT Pub. Date: Aug. 9, 1979

[51] Int. Cl.$^3$ .................. C07D 215/18; C07D 495/04
[52] U.S. Cl. ..................................... 546/114; 546/115; 546/116; 546/113; 546/180; 546/183; 546/80; 546/171; 546/89; 546/101
[58] Field of Search ............... 546/114, 115, 116, 113, 546/180, 183, 171, 89, 101, 80

[56] References Cited

U.S. PATENT DOCUMENTS 4,006,148  2/1977  Wehrmeister ...................... 260/289

OTHER PUBLICATIONS

Nickel et al., Chemical Abstracts, vol. 87, entry 23006s (1977).
Meth-Cohn et al., Tetrahedron Letters, No. 23, pp. 2045-2048 (1978).
C. Jones(Ed) "The Chemistry of Heterocyclic Compounds", vol. 32, Pt. 1 (1977) Quinolines, Wiley Publishers, N.Y., pp. 405-406, 408-410, 413, 415, 425-426, 431-433, 441, 444, 469, 602, 704-707, 709-711, 714-715, 717-720, 725-729, 731, 732 and 735.
Paulmier et al., Chemical Abstracts, vol. 88, 121019g, (1978).
Yoshikawa, Chemical Abstracts, vol. 56, entry 11567g (1962).
Klemm et al., J. of Heterocyclic Chemistry, vol. 13, No. 6, pp. 1197-1200 (1976).
Schneller, Int. J. Sulfur Chem., B, vol. 7, No. 4 (1972) "Thienopyridines", pp. 309-317.
Barker, Advances in Heterocyclic Chem., "The Thieonpyridines" (1977), pp. 117-118.
Giles., Chemical Abstracts, vol. 89, entry 129437.
Klemm et al., Chem. Abstracts, vol. 72, entry 90155t.
Drugs of the Future, vol. 11, pp. 196-197, 359, and 432-433 (1977).

Primary Examiner—John M. Ford
Attorney, Agent, or Firm—Lawrence Rosen

[57] ABSTRACT

Aromatic-α-halo-{b} fused pyridines are made by reacting an aromatic acetamide, acid halide and amide in particular proportions, with the acid halide always in excess. The process permits the production of compounds having a wide range of substituents, that are new compounds, and that are of value as intermediates in the synthesis of, for instance, pharmaceutical compounds.

14 Claims, No Drawings

FUSED PYRIDINES

This invention relates to aromatic {b} fused pyridines, that is to say compounds comprising a pyridine ring fused to another aromatic ring in a position such that one of the carbon atoms bonded to the nitrogen of the pyridine ring is part of the aromatic ring. These compounds have the formula

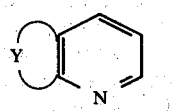

where Y are the atoms necessary to complete an aromatic ring. The aromatic ring may be monocyclic or polycyclic and may be carbocyclic, e.g. benzene or naphthalene, or heterocyclic, e.g. thiophen, furan, pyrrole or indole (including of course benzo-derivatives such as benzothiophen and benzofuran), and any or all rings in the compounds may carry one or more substituents. Examples are thienopyridines and quinolines.

Aromatic {b} fused pyridines are useful intermediates in the preparation of compounds having pharmaceutical and other utilities. It is generally desired that these compounds should carry one or more substituents, the substituents being chosen according to the desired end use of the compounds.

Various methods are known for making aromatic {b} fused pyridines and aromatic {c} fused pyridines. For instance one method of making a thienopyridine comprises starting from a pyridine and subjecting this to appropriate reactions so as to form a fused ring on it. However these reactions tend to be rather difficult to conduct, to give rather low yields and also it tends to be difficult to form thienopyridines having a range of substituents.

Another method of making aromatic pyridines comprises starting with an aromatic nucleus and subjecting it to condensation processes with other small molecules followed by cyclisation, in order to construct a fused pyridine moiety on to the existing homo- or heteroaromatic structure. However, these reactions in general tend to be rather difficult to conduct, often give poor yields and are of limited application.

There is a useful review of methods of making thieno {b} pyridines and thieno {c} pyridines in International Journal Sulphur Chemistry, B, volume 7, No. 4, 1972 pages 309 to 316 by Schneller, and more recently in Advances in Heterocyclic Chemistry 1977, 21, 65, by J. M. Barker.

Methods of making particular aromatic {c} fused pyridines have recently been described by Koyama et al in Chem. Pharm. Bull 1975, 23 (3) pages 497 to 500. In these methods an aromatic acetonitrile was reacted with dimethylformamide and phosphorus oxychloride using approximately equimolar quantities of the three components. Paulmier et al in J. Chem Research (S) 1977 pages 318 and 319 and in J. Chem. Research (M) 1977 pages 3660 to 3672 describe a similar process starting from β-thienyl acetonitrile, to form a thieno{c}pyridine. They also describe a modified process starting from an acetamido thiophen to produce thieno{b}pyridines of the formula

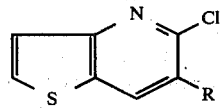

where R is H or CHO. The described process comprises reacting substantially equimolar amounts of acetamido thiophen and phosphorus oxychloride and a large excess of dimethylformamide and is said to give a mixture containing 23% of the compound where R is H, 5% of the compound where R is CHO and about 25% of other thiophen derivatives. Thus the method gives low yields of a mixture and is not satisfactory for commercial use. Also there is no suggestion that the method could be used for the production of compounds where either or both of the rings carry other substituents.

We have now discovered a new method for making thienopyridines, quinolines and other aromatic {b} fused pyridines which has the advantages that it can be carried out relatively easily in good yield and that it can be used to produce such compounds having a wide range of substituents, including substituents that render the compounds of particular use as intermediates in the production of pharmaceutical and other commercially useful compounds.

The compounds made by the method of the invention are aromatic-α-halo{b} fused pyridines, namely compounds in which there is a halo group on the carbon atom bonded to the nitrogen of the pyridine ring but which is not part of the fused aromatic ring, such as thieno-α-halopyridine and 2-haloquinolines. These compounds may carry one or more substituents in one or all rings. The invention permits the production of novel compounds.

According to the invention, an aromatic α-halo{b} fused pyridine is made by reacting an aromatic acetamide with an amide and with an inorganic acid halide, in a solvent, the amount of the acid halide being at least 2 moles per mole acetamide group and at least 1.5 moles, preferably at least 2 moles, per mole of the amide.

This method can readily be operated to give good yields of a wide variety of aromatic {b} fused pyridines.

Unless it is desired that the pyridine should be formyl substituted at the β position it is preferred to carry out the reaction using 0.8 to 2, preferably 0.9 to 1.5 and most preferably about 1, mole amide per mole acetamide group and using from 2 to 5, preferably 2.5 to 3.5 and most preferably about 3, moles of the acid halide per mole acetamide group. Halogenated hydrocarbons are preferred as the solvent. The reaction temperature is preferably from 70° to 200° C., most preferably 70° to 150° C. and the reaction is preferably conducted for from ½ to 15 hours, generally 2 to 8 preferably 4 to 6 hours. Normally it is conducted under reflux at atmospheric pressure and to give suitable reflux temperatures the solvent chosen is normally dichloroethane or tetrachloroethane. However the use of elevated pressure, e.g. as obtained by heating to the desired temperature in a sealed vessel, is sometimes advantageous.

If it is desired that the pyridine should be formyl substituted in the β-position it is preferred to carry out the reaction using at least 2 moles amide and at least 3 moles of the acid halide per mole acetamide group. Normally the amount of amide is from 2 to 6, preferably 2.5 to 4 and most preferably about 3 moles amide per mole acetamide group and the amount of the inorganic acid halide is preferably at least 5, but usually less than 15, moles per mole acetamide group.

Preferably the acid halide is used in such an excess that it can serve as the solvent so that other solvent is unnecessary. Accordingly the reaction is preferably conducted in the presence of at least 6 moles acid halide and in the absence of other solvent, about 7 moles often being preferred. The reaction temperature is normally from 70° to 200° C., preferably 70° to 150° C. and the reaction time is normally less than 12 hours, generally ½ to 6, preferably 1 to 4 hours. The reaction is preferably conducted either under reflux or in a sealed system. If desired it can be conducted under elevated pressure, but in most cases it is under atmospheric pressure.

The aromatic acetamide usually contains only one acetamide group in which event the reaction results in the formation of only one fused pyridine ring and the molar quantities discussed above are calculated on the basis of moles of aromatic acetamide. However more than one acetamide group may be present and may react in the process to form, for instance, an aromatic ring having fused onto it two separate pyridine rings. The molar quantities quoted above are then based on each mole of acetamide group so that, for instance, an aromatic diacetamide in which both acetamide groups are to react should be reacted with at least 4 moles of the acid halide or with at least 6 moles of the acid halide if a β-formyl group is required.

The process of the invention is based on a novel and surprising modification of the well known Vilsmeier or Vilsmeier-Haack reaction for the production of aromatic aldehydes or ketones. This reaction and literature references referring to it are discussed in The Merck Index 8th edition page 1223 and reference should be made to all those literature references, for further details of that reaction and of the materials that can be used in it. Any acid halide or amide or aromatic ring useful in the Vilsmeier reaction can be used in the present invention except that of course the aromatic ring must contain at least one acetamido group.

Amides suitable for use in the invention include the general formula $R^{11}{}_2NCOR^3$ where each radical $R^{11}$ is generally methyl but can be selected from alkyl (normally $C_{1-4}$) or aryl (e.g. phenyl) or the two radicals $R^{11}$ and the nitrogen to which they are bonded can form a heterocyclic ring, usually of 5 carbon atoms, and $R^3$ is hydrogen, alkyl, alkenyl, aryl or aralkyl. The group $R^3$ appears at the γ position of the pyridine ring. The preferred amide is dimethylformamide but others that may be used successfully include for example N-methylformanilide, N-formylpiperidine, and N,N-dimethylbenzamide.

The inorganic acid halide is preferably phosphorus oxychloride but others that may be used include phosphorus oxybromide, thionyl chloride, phosgene, phosphorus pentachloride and phosphorus pentabromide. The halogen of the inorganic acid halide appears at the α position of the pyridine ring.

The acetamido group in the aromatic acetamide generally has the formula $-NHCOCH_3$ but any acetamido group capable of entering into the reaction can be used and there are a wide variety of such groups. Generally such groups have the formula $-NR^6COCH_2R^5$ where $R^5$ is hydrogen, alkyl, usually $C_{1-4}$ preferably methyl, alkaryl or aryl and appears at the β position of the pyridine ring while $R^6$ is hydrogen or alkyl, usually $C_{1-4}$ preferably methyl. If $R^6$ is alkyl the product is in the form of a quaternary salt. If β-formyl substitution is required this is obtained using an acetamide wherein $R^5$ is hydrogen, together wth excess amide and halide as described above.

The aromatic compound can additionally be substituted by any substituents that are inert to the reaction, that is to say do not prevent the reaction happening. The inert substituents may have no effect on the reaction or may promote the reaction. The reaction involves fusion of the pyridine ring onto the aromatic ring at the carbon atom adjacent to the ring carbon atom on which the acetamido group is substituted. Generally therefore this adjacent carbon atom should be unsubstituted. However it may be substituted with a substituent that is labile, that is to say under the conditions of the reaction is driven from the position so as to permit the desired substitution to occur. Accordingly when saying, herein, that the ring is unsubstituted we mean that it is either totally unsubstituted or is substituted by a labile substituent. Inert substituents in other positions in the ring must not result in sufficient deactivation of the ring that reaction is prevented. Some deactivation may be tolerated and may be compensated for by, for example, increasing the reaction time, temperature or pressure. Typical deactivating substituents that it is desirable to avoid having in the ring include nitro, formyl, acyl, and related electron withdrawing groups in any position. Typical substituents that may be present in the ring include halo, alkyl, alkoxy, alkylthio, amino including both alkylamino and dialkylamino, aryl and alkaryl. Any alkyl group or alkyl moiety referred to herein preferably contains less than 8 carbon atoms, generally 1 to 4 carbon atoms and most preferably 1 to 2. Adjacent substituents in a ring may, together with the carbon atoms to which they are attached, form a heterocyclic ring containing one or more hetero atoms or a carbocyclic ring which may be saturated or unsaturated. The ring generally contains 5 to 7 members, usually 6.

Broadly the process of the invention preferably comprises the use of any acetamide of the formula

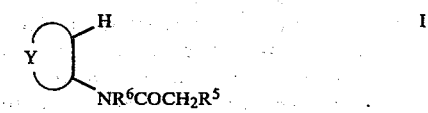

to produce a compound of the formula

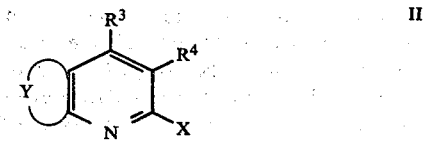

wherein $R^3$, $R^5$ and $R^6$ are as defined above, X is halo, $R^4$ is H, alkyl, aryl alkaryl, formyl or acyl, and Y represents the atoms (usually 3 to 4) necessary to complete an aromatic ring which may be carbocyclic (e.g. benzene) or heterocyclic (e.g. thiophen, furan or pyrrole) and which may contain substituents on some or all of its ring carbon atoms with suitable substituents typically being selected from halo, alkyl, alkoxy, alkylthio, monoalkylamino, dialkylamino, aryl or alkaryl or acetamido or adjacent substituents may form a saturated or unsaturated carbocyclic ring or a heterocyclic ring.

When Y represents a benzene ring compounds of formula III

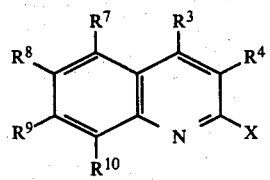

are made by reaction of a benzene derivative of formula IV

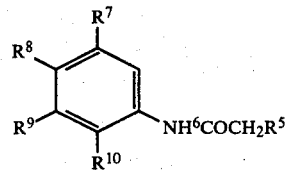

wherein $R^7$, $R^8$, $R^9$ and $R^{10}$ may be hydrogen, alkyl, alkoxy, alkylamino, dialkylamino, alkylthio, aryl or alkaryl, but if one of $R^7$, $R^8$, $R^9$ and $R^{10}$ (generally $R^8$ or $R^9$) is acetamido then a pyrido quinoline will be formed provided the adjacent ring carbon atom is either unsubstituted or substituted by a labile substituent. Thus broadly the aromatic acetamide is normally selected from acetanilides having up to 4 ring substituents and diacetanilides having up to 3 ring substituents.

The position of the fused pyridine ring will depend not only upon the substituents in the aromatic ring but, in heterocyclic rings, upon the position of the acetamido group with respect to the hetero atom.

In the case of thiophen if the acetamido group is in the 3-position and the 2 and 5-positions of the thiophen are blocked with, for example, alkyl, aryl or alkaryl or halo groups then the pyridine will be formed at the 3,4-position of the thiophen. If the thiophen is a 3-acetamido thiophen and the 2 and optionally also the 5-positions are unblocked then the pyridine ring will be substituted at the 2,3-positions, with the nitrogen of the pyridine being bonded to the 3-position of the thiophen. If the acetamido group is at the 2-position of the thiophen and if the 5-position is blocked, for example with halo, alkyl, aryl or alkaryl then the pyridine will be bonded to the thiophen at the 2,3-positions, with the nitrogen of the pyridine being bonded to the 2-position of the thiophen.

Accordingly, three different types of thienopyridines may be made in the invention. Whilst a wide variety of substituents may be present in the thienopyridines the preferred compounds made by the process of the invention have one of the general formulae V, VI or VII below:

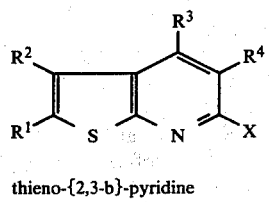

thieno-{2,3-b}-pyridine

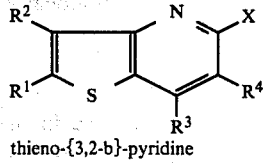

thieno-{3,2-b}-pyridine

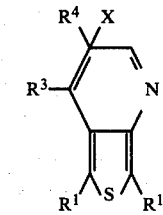

thieno-{3,4-b}-pyridine.

In these formulae $R^1$ and $R^2$ may be halo, alkyl, alkoxy, alkylthio, alkylamino, dialkylamino, aryl or alkaryl, $R^2$ may also be hydrogen, $R^3$ may be alkyl, aryl, aralkyl or hydrogen, $R^4$ may be alkyl, aryl, alkaryl, hydrogen, formyl or acyl, and X is halo, preferably bromo or chloro. In formulae V and VI $R^1$ and $R^2$ together with the carbon atoms to which they are attached may form a heterocyclic ring or a carbocyclic ring. The carbocyclic ring may be for instance cyclohexyl or phenyl. The heterocyclic ring may be pyridine, for instance an α-halo pyridine or α-halo-β-formylpyridine ring. In the compounds of formula VI $R^1$ may also be hydrogen.

Such compounds may be formed direct by the described reaction. Also compounds in whch $R^1$ and/or $R^2$ are hydrogen may be made by the described reaction to produce a compound in which $R^1$ and/or $R^2$ is halo and then subjecting the resultant compound to dehalogenation, for example by reaction with zinc and acetic acid.

Compounds of formulae V are generally made by reaction with a thiophen of formula VIII

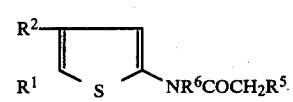

Compounds of formulae VI are made by reacting a thiophen of formula IX

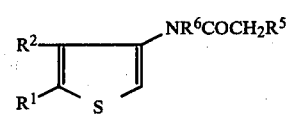

wherein $R^1$ can be as defined above or hydrogen.

Compounds of formulae VIII are made by reacting a thiophen of formula X

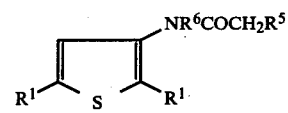

wherein the two radicals $R^1$ may be the same or different, the radical in the 5-position optionally being hydrogen.

When $R^1$ and $R^2$ are to form, with their adjacent ring carbon atoms, an α halo pyridine the starting thiophen should be a di-acetamidothiophen, for instance where $R^1$ or $R^2$ in formulae VIII, IX or X represents —NR$^6$COCH$_2$R$^5$.

The aromatic acetamides for use as starting materials in the invention, including the acetanilides of formula IV and the thiophens of formulae VIII, IX and X are generally known materials and those in which any particular combination of substituents are new can be made by methods known for the production of analogous compounds. In particular the acetamido thiophens may be made by a modified Beckmann re-arrangement as described by Cymerman-Craig et al Journal Chemical Society 1955 page 1071 to 1075.

Except for the compounds discussed above and disclosed by Paulmier, the compounds of formula II above including also the compounds of formula III, V, VI and VII, are novel compounds and so form a further part of this invention. Particularly preferred compounds according to the invention are those in which Y represents a thiophen ring that is optionally substituted, especially when the ring is a 3,4 ring as illustrated in, for instance, formula VII.

The novel compounds also include compounds readily obtainable from those discussed above. For example compounds of formula V wherein $R^1$ is hydrogen can readily be made by debromination of such compounds wherein $R^1$ is bromo.

Throughout this specification wherever reference is made to halo, the halogen atoms preferably are chlorine or bromine.

Typical reactions in which the novel compounds of the invention are valuable are illustrated as follows

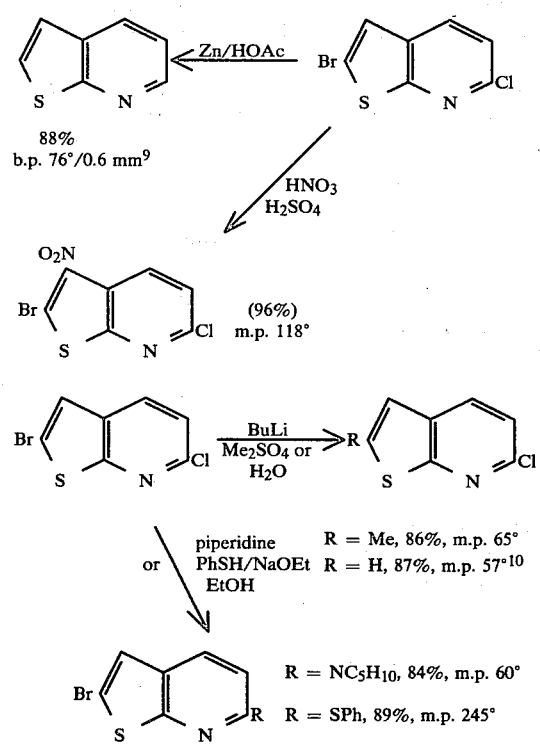

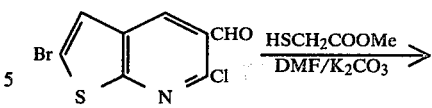
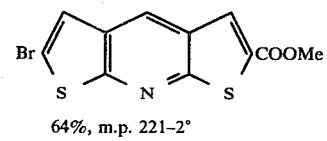

Corresponding reactions are of value where the starting thiophen is a thieno-{3,4-b}-pyridine and where the starting material is a quinoline or other novel compound according to the invention.

The following are some examples of the invention.

EXAMPLE 1

1 mole of 2-acetamido-5-bromothiophen was reacted with 1 mole dimethylformamide and 3 moles phosphorus oxychloride under reflux in tetrachloroethane for 3 hours at a temperature of 138° C. The compound of formula V in which $R^1$ represents bromo, X represents chloro, and $R^2$, $R^3$ and $R^4$ represent hydrogen was isolated in a yield of 66%. The remainder of the product was accounted for, mainly as unreacted starting material together with a small amount (ca 1%) of polymeric materials. The specified compound of formula V (2-bromo-6-chloro-thieno{2,3-b}-pyridine) was isolated from the crude product by chromatography on a short column of alumina using light petroleum spirit as eluant. The compound was recrystallised from ethanol and had a melting point of 116° C.

EXAMPLE 2

1 mole of 2-acetamido-5-bromothiophen was reacted with 3 moles dimethylformamide in 7 moles of phosphorus oxychloride at reflux, the large excess of phosphorus oxychloride serving both as reagent and as refluxing solvent. The reaction was continued for 1 hour. The reaction product consisted almost entirely of a compound of formula V wherein $R^4$ represents formyl, $R^2$ and $R^3$ represent hydrogen, $R^1$ represents bromo and X represents chloro. The product 2-bromo-6-chloro-thieno{2,3-b}pyridine-4-carboxaldehyde, was purified by recrystallisation from ethyl acetate and had a melting point of 170° C. The pure material was isolated in 66% yield.

Analysis found: C 34.702, H 1.188, N 5.255. $C_8H_3NOSBrCl$ requires: C 34.747, H 1.094, N 5.065.

EXAMPLES 3 to 23

The processes of Examples 1 and 2 were repeated using different acetamides, in which $R^5$, $R^6$ and all ring substituents other than those stated in the table are hydrogen. In Examples 3, 5, 7, 9, 11, 13, 15, 17, 19 and 21 the acetamide was reacted with 1 mole dimethylformamide and 3 moles $POCl_3$ in the presence of an inert solvent under reflux to produce the corresponding aromatic {b} fused pyridine in which $R^3$ and $R^4$ are hydrogen and X is chlorine. In Examples 4, 6, 8, 10, 12, 14, 16, 18, 20 and 22 the process of Example 2 was repeated using 3 moles dimethylformamide and 7 moles phosphorus oxychloride under reflux to produce the corresponding aromatic {b} fused pyridine in which $R^3$ is hydrogen, $R^4$ is CHO and X is chlorine.

In Example 23 the process was conducted by reacting the acetamide (1 mole) with 3 moles dimethylformamide and 5 moles $POCl_3$ in a sealed tube for 4 hours at 115°–120° C.

The starting materials, reaction conditions and end products are given in the Table below in which the solvent t is tetrachloroethane and the solvent d is dichloroethane.

TABLE

| Example | Starting Acetamide Formula | Starting Acetamide Substituent | Solvent | Reflux time (hours) | Product Formula | $R^4$ | Yield (%) | M.p. or b.p./mm °C. |
|---|---|---|---|---|---|---|---|---|
| 3 | IV | $R_9$ = MeO | t | 4 | III | H | 73 | 145/0.6 |
| 4 | IV | $R_9$ = MeO | — | 4 | III | CHO | 89 | 190 |
| 5 | IV | $R_9$ = Me | t | 6 | III | H | 59 | 120/0.5 |
| 6 | IV | $R_9$ = Me | — | 6 | III | CHO | 64 | 142 |
| 7 | IV | $R_8 = R_9$ = MeO | t | 4 | III | H | 69 | 72–74 |
| 8 | IV | $R_8 = R_9$ = MeO | — | 2 | III | CHO | 72 | 215 |
| 9 | IV | $R_8 = R_9 = R_{10}$ = MeO | t | 6 | III | H | 71 | 92–93 |
| 10 | IV | $R_8 = R_9 = R_{10}$ = MeO | — | 1.5 | III | CHO | 92 | 149.5 |
| 11 | VIII | $R_1$ = Br | t | 12 | V | H | 66 | 115–116 |
| 12 | VIII | $R_1$ = Br | — | 4 | V | CHO | 66 | 170 |
| 13 | VIII | $R_1$ = Me | d | 6 | V | H | 79 | 65 |
| 14 | VIII | $R_1$ = Me | — | 3 | V | CHO | 62 | 127 |
| 15 | VIII | $R_1 = R_2$ = Me | d | 5 | V | H | 72 | 91 |
| 16 | VIII | $R_1 = R_2$ = Me | — | 2 | V | CHO | 73 | 157 |
| 17 | VIII | $R_1 + R_2 = -(CH_2)_4-$ | d | 4 | V | H | 79 | 64.5 |
| 18 | VIII | $R_1 + R_2 = -(CH_2)_4-$ | — | 2 | V | CHO | 88 | 145 |
| 19 | XI | all H | d | 4 | VI | H | 70 | 63–64 |
| 20 | XI | all H | — | 1.5 | VI | CHO | 72 | 122 |
| 21 | X | $R_1 = R_1$ = Me | d | 6 | VII | H | 52 | 158 |
| 22 | X | $R_1 = R_1$ = Me | — | 2.5 | VII | CHO | 39 | 146 |
| 23 | IV | all H | — | — | III | CHO | 81 | — |

The compounds of Examples 19 and 20 are known and had melting points corresponding to the known value. All the other compounds gave correct analytical and spectral data (by infra-red, protonmagnetic resonance, carbon-13 magnetic resonance, mass spectroscopy).

EXAMPLE 24

N,N'-diacetyl-metaphenylene diamine, dimethyl formamide and phosphorus oxychloride were reacted in the molar proportions 1:6:14 for 4 hours under reflux to give a 92% yield of 2,6-dichloro-3,7-dichloro-3,7-diformyl pyrido{2,3-f}quinoline.

What is claimed is:

1. In the synthesis of an aromatic-α-halo[b]fused pyridine by reacting an N-substituted acetamide with an N-substituted formamide and an inorganic acid halide in a solvent, wherein the substituent on the N atom of the acetamide is an aromatic ring in which the ring carbon atom adjacent to the ring carbon atom substituted by the N atom is unsubstituted or is substituted by a labile substituent and wherein the carbon atom adjacent the CO group of the acetamide group carries at least two hydrogen atoms, the improvement consisting of reacting the acid halide in an amount of at least 2 moles per mole acetamide group and at least 1.5 moles per mole N-substituted formamide.

2. A process according to claim 1, characterized in that the amount of N-substituted formamide is 0.8 to 2 moles and the amount of acid halide is 2 to 5 moles per mole acetamide group.

3. A process according to claim 1, characterized in that the amount of N-substituted formamide is from 0.9 to 1.5 moles and the amount of acid halide is from 2.5 to 3.5 moles per mole acetamide group.

4. A process according to claim 2 or claim 3, characterized in that the solvent is a halogenated hydrocarbon.

5. A process according to claim 1, for the production of an aromatic α-halo-β-formyl [b] fused pyridine characterized in that the amount of N-substituted formamide is from 2 to 6 moles and the amount of acid halide is at least 3 moles per mole acetamide group.

6. A process according to claim 5 characterized in that the amount of N-substituted formamide is 2.5 to 4 moles and the amount of acid halide is at least 5 moles per mole acetamide group.

7. A process according to claim 5 or claim 6 characterized in that the solvent is the acid halide.

8. A process according to claim 1 characterized in that it is conducted at a temperature of 70° to 200° C.

9. A process according to claim 1 characterized in that the acid halide is phosphorus oxychloride.

10. A process according to claim 1 characterized in that the N-substituted formamide has the formula $R_2^{11}NCOR^3$ wherein $R^3$ is hydrogen and each group $R^{11}$ is selected from alkyl or aryl or the two radicals $R^{11}$ form a heterocyclic ring, and the N-substituted acetamide has the formula

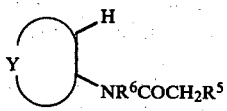

wherein R[5] represents hydrogen, alkyl, alkaryl or aryl and R[6] represents hydrogen or alkyl, Y represents 3 or 4 atoms necessary to complete an aromatic ring which may be carbocyclic or heterocyclic selected from thiophen, furan or pyrrole and which may contain substituents on some or all of its ring carbon atoms with suitable substituents typically being selected from halo, alkyl, alkoxy, alkylthio, monoalkylamino, dialkylamino, aryl or alkaryl or acetamido or adjacent substituents may form a saturated or unsaturated carbocyclic ring or a pyridine ring, and wherein the alkyl group or alkyl moiety of a substituent contains less than 8 carbon atoms and the aryl group or aryl moiety of a substituent is phenyl.

11. A process according to claim 10 characterized in that the formamide is dimethylformamide.

12. A process according to claim 10 characterized in that the aromatic ring substituted on the N position in the acetamide is a thiophen ring optionally substituted by one or more substituents selected from halo, alkyl, alkoxy, alkylthio, alkylamine, dialkylamine, aryl, alkaryl or acetamide or adjacent substituents on the ring, together with the carbon atoms to which they are attached, form a carbocyclic or pyridine group.

13. A process according to claim 10 characterized in that the N-substituted acetamide is an acetanilide in which the ring is optionally substituted by one or more substituents selected from halo, alkyl, alkoxy, alkylthio, mono alkylamine, dialkylamine, aryl, alkaryl or acetamide or adjacent substituents on the ring, together with the carbon atoms to which they are attached, form a carbocyclic or pyridine group.

14. A process according to claim 1 characterized in that the N-substituted acetamide has the formula

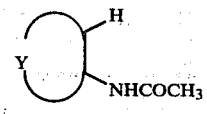

and the aromatic ring contains no additional substituents or one or more substituents selected from alkyl, alkoxy, halo and acetamido or two adjacent positions in the aromatic ring are substituted to form a carbocyclic ring, Y represents 3 or 4 atoms necessary to complete an aromatic ring which may be carbocyclic or heterocyclic thiophen, furan or pyrrole and which may contain substituents on some or all of its ring carbon atoms with suitable substituents typically being selected from halo, alkyl, alkoxy, alkylthio, monoalkylamino, dialkylamino, aryl or alkaryl or acetamido or adjacent substituents may form a saturated or unsaturated carbocyclic ring or a pyridine ring.

* * * * *